(12) United States Patent
Kadam et al.

(10) Patent No.: US 11,292,775 B2
(45) Date of Patent: Apr. 5, 2022

(54) EFFICIENT PROCESS FOR THE SYNTHESIS OF 2-[2-(1-CHLOROCYCLOPROPYL)-3-(2-CHLOROPHENYL)-2-HYDROXYPROPYL]-2,4-DIHYDRO-3H-1,2,4-TRIAZOLE-3-THIONE(PROTHIOCONAZOLE) AND ITS INTERMEDIATES

(71) Applicant: GSP CROP SCIENCE PVT. LTD., Ahmedabad (IN)

(72) Inventors: Subhash Rajaram Kadam, Ahmedabad (IN); Nilesh Jani, Ahmedabad (IN); Ravindra Shinde, Ahmedabad (IN); Kenal V. Shah, Ahmedabad (IN); Bhavesh V. Shah, Ahmedabad (IN); Ajit Singh Gujral, Ahmedabad (IN); Ganganarasaiah Byregowda, Bangalore (IN); Ganadi Sivaiah, Bangalore (IN); Jivan Dhanraj Pawar, Bangalore (IN); Hari Narayan Pati, Bangalore (IN)

(73) Assignee: GSP CROP SCIENCE PVT. LTD., Ahmedabad (IN)

( * ) Notice: Subject to any disclaimer, the term of this patent is extended or adjusted under 35 U.S.C. 154(b) by 0 days.

(21) Appl. No.: 16/955,469

(22) PCT Filed: Dec. 20, 2018

(86) PCT No.: PCT/IB2018/060427
§ 371 (c)(1),
(2) Date: Jun. 18, 2020

(87) PCT Pub. No.: WO2019/123368
PCT Pub. Date: Jun. 27, 2019

(65) Prior Publication Data
US 2020/0369627 A1 Nov. 26, 2020

(30) Foreign Application Priority Data

Dec. 21, 2017 (IN) .............................. 201721046132

(51) Int. Cl.
*C07D 249/12* (2006.01)
*B01J 31/02* (2006.01)

(52) U.S. Cl.
CPC ........ *C07D 249/12* (2013.01); *B01J 31/0215* (2013.01)

(58) Field of Classification Search
CPC ................................................... C07D 249/12
See application file for complete search history.

(56) References Cited

U.S. PATENT DOCUMENTS

2003/0013890 A1  1/2003  Hupperts et al.

FOREIGN PATENT DOCUMENTS

| CN | 106986838 | 7/2017 |
| DE | 4030039 | 3/1992 |

*Primary Examiner* — Shawquia Jackson
(74) *Attorney, Agent, or Firm* — Volpe Koenig

(57) ABSTRACT

The present invention relates to an improved and efficient process for the synthesis of 2-[2-(1-chlorocyclopropyl)-3-(2-chlorophenyl)-2-hydroxypropyl]-2,4-dihydro-3H-1,2,4-triazole-3-thione, compound of formula (I) (Prothioconazole). The present invention more particularly relates to an improved process for manufacturing of 2-(1-chloro-cycloprop-1-yl)-3-(2-chloro phenyl)-2-hydroxy propyl-1-hydrazine (compound of formula III) and 2-[2-(1-chlorocyclopropyl)-3-(2-chlorophenyl)-2-hydroxypropyl]-1,2,4-triazolidine-3-thione (compound of formula II) which are mainly used for synthesis of Prothioconazole which is knows as an active compound with microbicidal fungicidal properties.

13 Claims, No Drawings

EFFICIENT PROCESS FOR THE SYNTHESIS OF 2-[2-(1-CHLOROCYCLOPROPYL)-3-(2-CHLOROPHENYL)-2-HYDROXYPROPYL]-2,4-DIHYDRO-3H-1,2,4-TRIAZOLE-3-THIONE (PROTHIOCONAZOLE) AND ITS INTERMEDIATES

CROSS REFERENCE TO RELATED APPLICATIONS

This application is a 35 USC § 371 national stage of International Application No. PCT/IB2018/060427, which was filed Dec. 20, 2018 and claims the benefit of IN Patent Application No. 201721046132, filed Dec. 21, 2017, both of which are incorporated herein by reference as if fully set forth.

FIELD OF INVENTION

The present invention relates to an improved and efficient process for the synthesis of 2-[2-(1-chlorocyclopropyl)-3-(2-chlorophenyl)-2-hydroxypropyl]-2,4-dihydro-3H-1,2,4-triazole-3-thione (Prothioconazole). The present invention more particularly relates to an improved process for manufacturing of intermediates viz. 2-(1-chloro-cycloprop-1-yl)-3-(2-chloro phenyl)-2-hydroxy propyl-1-hydrazine and 2-[2-(1-chlorocyclopropyl)-3-(2-chlorophenyl)-2-hydroxypropyl]-1,2,4-triazolidine-3-thione, used in the synthesis of Prothioconazole, an active ingredient having fungicidal properties.

BACKGROUND OF THE INVENTION

Prothioconazole, 2-[(2RS)-2-(1-chlorocyclopropyl)-3-(2-chlorophenyl)-2-hydroxypropyl]-2H-1,2,4-triazole-3 (4H)-thione, the structure of which is shown below, is used as a fungicide to treat infected crops. The molecule itself was first described in U.S. Pat. No. 5,789,430. The structure is reproduced below:

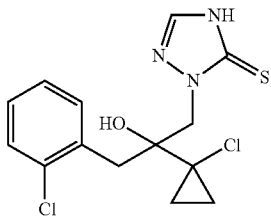 [SMILES: OC(Cc1ccccc1Cl)(Cn1nc[nH]c1=S)C1(Cl)CC1]

U.S. Pat. No. 4,913,727 describes a process for producing 1-chloro-2-(1-chlorocyclopropyl)-3-(2-chlorophenyl)propan-2-ol using a highly inflammable solvent such as diethyl ether. This patent also discloses reaction of 1-chloro-2-(1-chlorocyclopropyl)-3-(2-chlorophenyl)propan-2-ol with 1,2-4-triazole under basic condition. The disadvantage of this process is that under basic condition, 1,2,4-triazole undergoes isomerization, resulting in the formation of corresponding regio-isomers as an impurity.

U.S. Pat. No. 5,146,001 describes a process for producing ketone using highly toxic and expensive palladium complex bis(triphenylphosphine)-palladium (II) chloride along with zinc dust. This patent discloses the use of highly unstable acid chloride (1-chlorocyclopropane-carbonyl chloride) at a higher temperature such as 150° C. This patent also discloses the preparation of oxirane using highly expensive trimethylsulphoxonium halides or trimethylsulphoxonium methyl sulphate along with strong bases such as potassium hydroxide, potassium tert-butoxide and sodium methoxide in various solvents such as dimethyl sulphoxide, acetonitrile, etc. Final Prothioconazole obtained by this process was purified by column chromatography, which is not a suitable option for manufacturing at industrial scale.

U.S. Pat. No. 5,099,040 discloses process for producing mixture of 1-chloro-2-(1-chlorocyclopropyl)-3-(2-chlorophenyl)propan-2-ol and 2-(2-chlorobenzyl)-2-(1-chlorocyclopropyl)oxirane using a mixture of various solvent particularly a mixture of toluene and THF, which is the disadvantage of this process as separation of toluene from THF is not cost effective process on an industrial scale.

U.S. Pat. No. 6,262,276 discloses a process for producing thiosemicarbazide, which then admixed with isobutyl formate and formic acid to get Prothioconazole. Formation of an isomeric impurity during the reaction of hydrazine derivatives and thiocyanate in basic condition is a disadvantage of this method. Moreover, expensive and hazardous reagents such as n-butyllithium along with sulphur were used to construct triazolidinethione ring in 2-(1-chlorocyclopropyl)-1-(2-chlorophenyl)-3-(1,2,4-triazol-1-yl)-propan-2-ol.

WO99/18087 describes the process for preparation of 2-(1-chloro-cycloprop-1-yl)-1-(2-chloro-phenyl)-3-(4,5-dihydro-1,2,4-triazole-5-thiono-1-yl)-propan-2-ol 2-(1-Chloro-cycloprop-1-yl)-3-(2-chloro phenyl)-2-hydroxy propyl-1-hydrazine can be prepared by reacting 3-chloro-2-(1-chloro cycloprop-1-yl)-1-(2-chloro phenyl)-propan-2-ol with hydrazine hydrate in the presence of an inert organic solvents, such as alcohol, ether or nitrile. The reaction of resulting 2-(1-chloro-cycloprop-1-yl)-3-(2-chloro phenyl)-2-hydroxy propyl-1-hydrazine with formaldehyde and alkali metal thiocyanate or ammonium thiocyanate to get 2-(1-chloro cycloprop-1-yl)-1-(2-chloro phenyl)-2-hydroxy-3-(1,2,4-triazolidine-5-thiono-1-yl)-propane, which in turn reacts with oxygen in the presence of sulphur and potassium hydroxide to obtain Prothioconazole. 2-(1-Chloro-cycloprop-1-yl)-3-(2-chloro phenyl)-2-hydroxy propyl-1-hydrazine in its free state is relatively unstable, and hence contributes to lower yield in the subsequent stages.

US2003/013890 discloses a process for preparation of 2-(1-chloro-cycloprop-1-yl)-3-(2-chlorophenyl)-2-hydroxypropyl-1-hydrazine using hydrazine hydrate in a mixture of toluene and acetonitrile. Hydrochloric gas is employed to prepare hydrochloride salt of 2-(1-chloro-cycloprop-1-yl)-3-(2-chlorophenyl)-2-hydroxypropyl-1-hydrazine. Synthesis of 2-(1-chlorocycloprop-1-yl)-1-(2-chlorophenyl)-2-hydroxy-3-(1,2,4-triazolidine-5-thiono-1-yl)-propane involves the use of alkali metal hydroxides such as lithium hydroxide, sodium hydroxide, and potassium hydroxide in presence of water and ethyl acetate, leading the formation of 10-15% impurity, which causes low yield. Use of ferric chloride for aromatization at the last stage may lead to high iron content in the final product.

Problem Identified

The present invention deals with various factors associated with process improvement and process optimization of Prothioconazole (hereinafter referred as a compound of formula I). According to process disclosed in US2003/013890, 2-(1-chloro-cycloprop-1-yl)-3-(2-chlorophenyl)-2-hydroxypropyl-1-hydrazine (hereinafter referred as compound of formula III) was prepared by reacting 2-(1-chloro-cycloprop-1-yl)-2-(2'-chloro-benzyl)-oxirane of the formula (II), if appropriate in a mixture with 3-chloro-2-(1-chloro-cycloprop-1-yl)-1-(2-chlorophenyl)-propan-2-ol (hereinafter referred as compound of formula IV) with hydrazine hydrate in presence of mixture of aromatic hydrocarbons such as mixture of toluene and acetonitrile. It is found that reaction was incomplete and sluggish when toluene used as a solvent. This process is neither scaled up friendly nor cost-effective at industrial scale. In the present invention, the process that used single solvent has been developed.

According to Comparative example A [step (a)] reported in US2003/013890, 2-(1-chloro-cycloprop-1-yl)-3-(2-chlorophenyl)-2-hydroxypropyl-1-hydrazine (hereinafter referred as compound of formula III) was prepared by heating the mixture of 3-chloro-2-(1-chlorocycloprop-1-yl)-1-(2-chlorophenyl)-propan-2-ol (hereinafter referred as compound of formula IV) with hydrazine hydrate at 100° C. under an atmosphere of nitrogen.

The process reported in US2003/013890 for the preparation of 2-(1-chloro-cycloprop-1-yl)-3-(2-chlorophenyl)-2-hydroxypropyl-1-hydrazine involves the use of hydrazine hydrate at 100° C. which is not industrially viable option. This process also described use of acetonitrile for recrystallization which results into poor yield as compound is moderately soluble in acetonitrile. Moreover, use of 2-(1-chloro-cycloprop-1-yl)-3-(2-chlorophenyl)-2-hydroxypropyl-1-hydrazine without its hydrochloride salt in next step leads to many impurities.

US2003/013890 discloses the use of water along with ethyl acetate under strongly basic condition for the synthesis of 2-(1-chlorocycloprop-1-yl)-1-(2-chlorophenyl)-2-hydroxy-3-(1,2,4-triazolidine-5-thiono-1-yl)-propane (hereinafter referred as compound II) via in situ preparation of hydrazone (hereinafter referred as compound IIa), which is quite unstable under basic reaction conditions. Low purity and low yield are major disadvantages of this Step. Moreover, present inventors have overcome this problem by using the mild organic base in a suitable solvent.

Comparative example A [step (b)] reported in US2003/013890 discloses the use of methyl tert-butyl ether, paraformaldehyde for the synthesis of 2-(1-chlorocycloprop-1-yl)-1-(2-chlorophenyl)-2-hydroxy-3-(1,2,4-triazolidine-5-thiono-1-yl)-propane (hereinafter referred as compound II).

The Product obtained by this process is less pure. Purification of compound II obtained by this method using dichloromethane leads to low yield. The compound of the formula (II) is used in the next step without purification, affecting the purity and yield of final Prothioconazole. The present invention demonstrates the process for purification of the compound of formula (II). Purification leads to high quality and high purity (98% area by HPLC) of Prothioconazole.

According to process reported in US2003/013890, Prothioconazole was prepared by aromatization of compound of formula (II) using the catalytic amount of iron (III) chloride in presence of expensive solvent such as ethanol or mixture of ethanol and toluene in acidic condition. Use of expensive solvents such as ethanol or use of a mixture of ethanol and toluene may not be feasible options on a commercial scale. Moreover, use of the iron catalyst in the last stage of synthesis may lead to higher level of metal content in the final Active Ingredient.

According to comparative example A [Step (c)] reported in US2003/013890, Prothioconazole was prepared by aromatization of compound of formula (II) using stream of air in presence of potassium hydroxide and catalytic amount of sulphur powder in toluene at 70° C. Product obtained by this process is less pure (71% by HPLC). Therefore, this process is not appropriate at industrial scale.

Solution Provided by the Present Invention

An extensive research has been conducted by the present inventors to solve the above mentioned problems. As a result, surprisingly a method has been developed for producing a compound of formula (I) having consistent purity and yield. The method comprises reacting a compound of formula (II) with various oxidizing agents or Lewis acids in the presence of a solvent or mixture of solvents. It has also been demonstrated that the compound of the formula (II) can be readily aromatized to a compound of the formula (I) in a suitable solvent or mixture of solvents in presence of charcoal without using any oxidizing agent. The present inventors have surprisingly, found that rate of conversion of a compound of the formula (II) to a compound of the formula (I) depends on the quantity of charcoal used. The present inventors have further found that aromatization without using any oxidizing agent or Lewis acid is very cost-effective and giving good quality of the product.

According to the process reported in US2003/013890, a compound of the formula (II) can be prepared from the compound of the formula (III) using alkali metal hydroxide in presence of ethyl acetate in an aqueous medium. The present inventors herein report the use of organic bases over inorganic bases for manufacturing of compound of the formula (II) in halogenated solvents. The process of the present invention used for the preparation of a compound of the formula (II) is very simple, scalable, and reproducible at a higher scale. Very high purity of the compound of the formula (II) is achieved by recrystallization in different alcoholic solvents. The purity of the compound of formula (II) thus achieved by this process is more than 98% area by HPLC. High-pure compound of the formula (II) solves many problems associated with the use of various oxidising agents or Lewis acid for aromatization and leads to Prothioconazole in high purity and good-to-excellent yield.

The present inventors have also found that compound (I), compound (II), and compound (III) can be produced in good-to-high yield. Compound (III) can be prepared by treating a compound of formula (IV) with hydrazine hydrate in a single solvent. The compound of the formula (III) can be isolated as its hydrochloride salt with excellent purity.

Prothioconazole prepared by the process of the present invention is very simple, robust, scalable, high yielding, and easily reproducible at industrial scale. Solvents and reagents involved in the process disclosed in the present invention are commercially available, non-hazardous and environment friendly and cheap.

OBJECTS OF THE INVENTION

It is an object of the present invention to provide an improved and efficient process for the preparation of Prothioconazole of the formula (I), compound of the formula (II), and compound of the formula (III) in high purity and good yield.

It is another objective of the present invention to provide a simple, non-hazardous, scalable, and high yielding process for the preparation of compound of the formula (I), compound of the formula (II), and compound of the formula (III), wherein all impurities present are below their threshold levels.

It is another object of the present invention to provide a process for preparation of a compound of formula (III) from a compound of formula (II), objective of this invention is to using a single solvent which can be recovered and reuse.

It is yet another objective of the present invention to provide an excellent method for purification of the compound of the formula (II) using various alcoholic solvents to get >98% purity by HPLC.

SUMMARY OF THE INVENTION

According to an aspect of the present invention there is provided a process for the preparation of compound of formula (I)

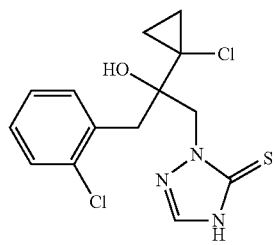

Compound-I comprising the steps of:
i) Reacting compound of the formula (IV) with hydrazine hydrate in alcoholic solvent to obtain compound of the formula (III);
ii) Isolating compound of formula (III) obtained in step i) in its salt form selected from hydrochloride salt, hydrobromide salt, sulphate salt;

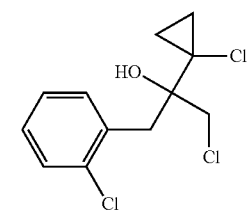

Compound-IV

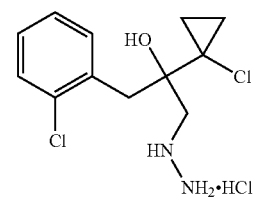

Compound-III iii) Reacting compound of the salt form of formula (III) obtained in step (ii) with aqueous formaldehyde solution in presence of a suitable solvent or a mixture of solvents and organic base at temperature between −5 and 35° C. to obtain compound of the formula (IIa), which on treatment with thiocyanate in presence of a catalyst and solvent at temperature between −5 and 35° C. to obtain crude compound of formula (II);

[Compound-IIa and Compound-II structures]

iv) Purifying crude compound of the formula (II) obtain in step iii) using alcoholic solvents;
v) Aromatization or oxidizing compound of the formula (II) obtained in step (iv) in presence of a suitable solvent or a mixture of solvents at a temperature between −10 and 75° C. to obtain a crude compound of formula (I);
vi) Purifying crude compound of the formula (I) obtained in step v) using suitable solvents or mixtures of suitable solvents.

DETAILED DESCRIPTION OF THE INVENTION

The present invention relates to an improved and efficient process for the synthesis of a compound of the formula (I). The present invention further relates to a novel and improved process for manufacturing of compound of the formula (II) and a compound of the formula (III).

In an embodiment of the present invention, there is provided a process for the preparation of Prothioconazole, compound of the formula (I).

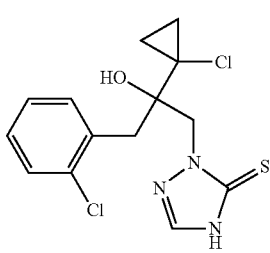

Compound-I comprising the steps of:
a) Oxidation or aromatization of compound of the formula (II) to compound of the formula (I). Aromatization can be conducted in following approaches.

In an embodiment of the present invention aromatization of compound of the formula (II) to compound of the formula (I) involves aromatization in presence of oxidizing agent in a suitable solvent or mixture of solvents.

In another embodiment of the present invention aromatization of compound of the formula (II) to compound of the formula (I) involves acid catalyzed aromatization in presence of oxidizing agent in a suitable solvent or mixture of solvents.

Acid is selected from the group consisting of hydrochloric acid, hydrobromic acid, acetic acid, benzoic acid, substituted benzoic acid, trifluoroacetic acid, and formic acid.

Solvents used in the present invention are selected from the group consisting of chlorinated hydrocarbons such as dichloromethane (DCM), ethylene dichloride (EDC), chloroform, and carbon tetrachloride; esters such as ethyl acetate, isopropyl acetate, and butyl acetate; polar protic solvents such as methanol, ethanol, n-propanol, isopropyl alcohol, n-butyl alcohol, tert-butyl alcohol, and n-pentanol, preferably methanol; polar aprotic solvents such as dimethyl sulfoxide (DMSO), N,N'-dimethylacetamide (DMAC), N,N'-dimethyl formamide (DMF), 2-methyl pyrolidinone (NMP), and hexamethylphosphoramide (HMPA); ethers or cyclic ethers such as tetrahydrofuran (THF), 1,4-Dioxane and methyl tert.-butyl ether (MTBE); nitrile such as acetonitrile or mixtures thereof.

Oxidizing agents are selected from the group consisting of hydrogen peroxide, m-chloro perbenzoic acid (m-CPBA), oxone, tert-butyl hydrogen peroxide (TBHP), copper sulphate, sodium nitrite, n-butyl nitrite, and tert-butyl nitrite.

In another embodiment of the present invention aromatization of compound of the formula (II) to compound of the formula (I) involves use of Lewis acid in a solvent or mixture of solvents compatible with Lewis acids.

Lewis acid is selected from the group consisting of aluminium chloride, stannous chloride, stannic chloride, titanium tetrachloride, boron trifluoride diethyl etherate, boron THF complex, zinc chloride to obtain compound of the formula (I).

In another embodiment of the present invention cost-effective oxidation or aromatization of the compound of the formula (II) to compound of the formula (I) can be carried out in a single alcoholic solvent or mixture of alcoholic solvents in presence of activated charcoal. The reaction is carried out at temperature between −10 and 75° C., preferably between 25 and 45° C.

In yet another embodiment of the present invention oxidation or aromatization of the compound of the formula (II) to compound of the formula (I) can be carried out in the presence of oxygen without using activated charcoal in suitable solvents.

In yet another embodiment crude compound of the formula (I) is purified using suitable solvents or mixtures of suitable solvents at temperature ranges from −5° C. and 82° C. Suitable solvent used for purification of compound of formula (I) is selected from non-polar hydrocarbon; mixture of non-polar hydrocarbon such as pentane, hexanes, heptane, octane; polar protic solvents such as methanol, ethanol, isopropyl alcohol, n-butyl alcohol, tert-butyl alcohol, pentanol; mixture of non-polar hydrocarbons with polar protic solvents.

b) Reaction of compound of the formula (III) with aq. formaldehyde solution in presence of organic bases in aromatic hydrocarbons to obtain in situ formation of compound of the formula (IIa), which in turn on treatment with thiocyanate such as sodium thiocyanate, potassium thiocyanate, and ammonium thiocyanate, preferably, ammonium thiocyanate in presence of catalyst such as sodium hydrogen sulphite, potassium hydrogen sulphate, and sodium hydrogen sulphate, preferably, potassium hydrogen sulphate at temperature between −5 and 35° C. to obtain a compound of formula (II). Various solvents employed for this conversion are selected from the group consist of chlorinated hydrocarbons such as dichloromethane (DCM), dichloroethane, ethylene dichloride (EDC), chloroform, and carbon tetrachloride, preferably dichloromethane or dichloroethane; esters selected from ethyl acetate, butyl acetate, and isopropyl acetate; aromatic hydrocarbons selected from toluene, xylene and chloro benzene; polar protic solvents selected from alcohols such as methanol, ethanol, n-propanol, isopropyl alcohol, n-butyl alcohol, tert-butanol, and n-pentanol; polar aprotic solvents selected from dimethyl sulfoxide (DMSO), N,N'-dimethylacetamide (DMAC), N,N'-dimethyl formamide (DMF), 2-methyl pyrolidinone (NMP), and hexamethylphosphoramide (HMPA); ethers or cyclic ether selected from tetrahydrofuran (THF), 1,4-dioxane and methyl tert.-butyl ether (MTBE), and nitrile such as acetonitrile or mixtures thereof and one or more organic bases selected from pyridine, N-methyl morpholine, triethylamine (TEA), diisopropylethylamine, 1,8-diazabicyclo [5.4.0] undec-7-ene (DBU), 1,4-diazabicyclo [2.2.2] octane (DABCO), sodium acetate, and potassium acetate, imidazole, preferably N,N-diisopropylethylamine. The reaction is carried out at temperature between −5 and 35° C.

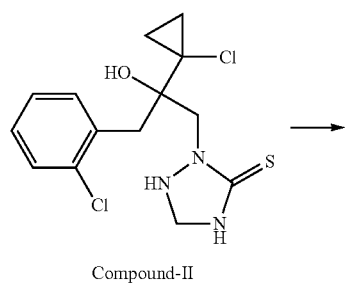

Compound-II

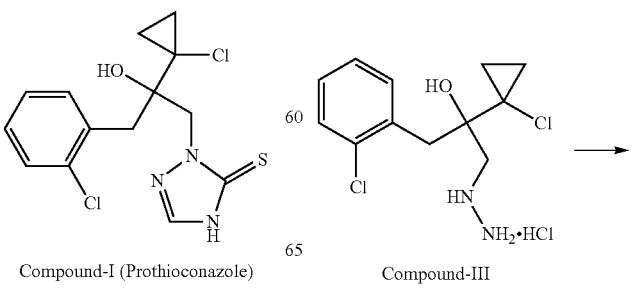

Compound-I (Prothioconazole)　　Compound-III

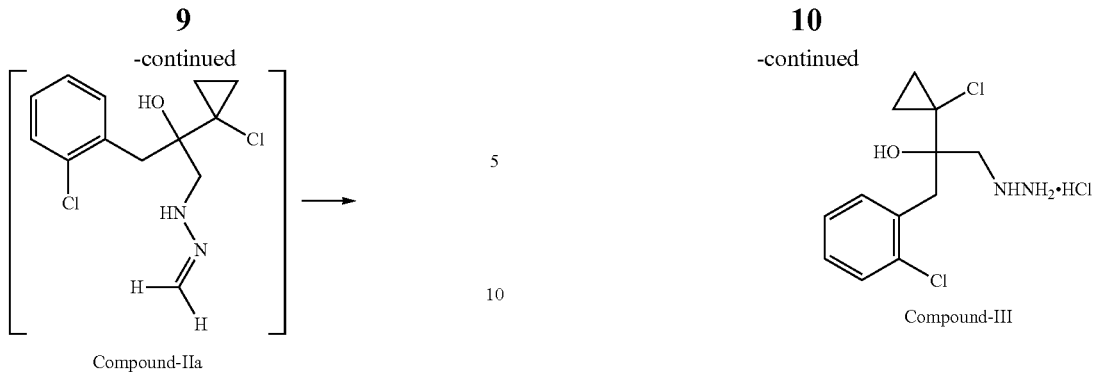

Compound-IIa

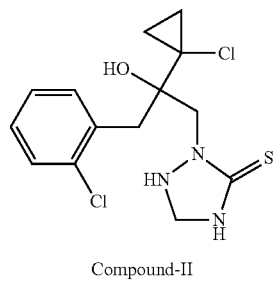

Compound-II

In yet another embodiment crude compound of the formula (II) can be further purified by standard methods, for example, by recrystallization using a suitable solvent or mixtures of suitable solvents at temperature ranges from −5° C. and 82° C., preferably between 20° C. and 50° C. In an embodiment crude compound of formula (II) is dissolved in suitable solvent at higher temperature say 82° C. and then cooled to room temperature and then further cooled to −5° C. to get good yield. Suitable alcoholic solvent used for purification of compound of formula (II) is selected from straight chain or branched chain alcohol such as methanol, ethanol, isopropyl alcohol, n-butyl alcohol, tert-butyl alcohol, pentanol. Crude compound of the formula (II) is purified using methanol preferably.

c) Reaction of compound of the formula (IV) with hydrazine hydrate in alcoholic solvents straight or branched chain alcohols selected from methanol, ethanol, isopropyl alcohol, n-butyl alcohol and tert-butanol to obtain compound of formula (III). The reaction is carried out at temperature between 75° C. and 85° C., preferably, between 75 and 80° C. Product is purified by forming hydrochloride salt, hydrobromide salt, or sulphate salt, preferably, hydrochloride salt. The reaction is carried out at a temperature between −5° C. and 30° C., preferably, between 20 and 30° C. The agent used for salt formation of compound of formula (III) is selected from hydrogen chloride gas, hydrochloric acid, hydrobromic acid, sulphuric acid preferably hydrogen chloride gas.

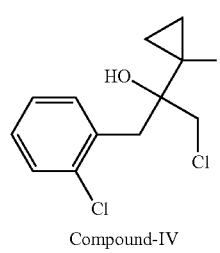

Compound-IV

Compound-III

In an embodiment of the present invention, step-a, aromatization can proceed in the following possible ways. First approach involves aromatization in presence of oxidizing agents optionally in the presence of acid. In this case, acid used is hydrochloric acid and oxidizing agents employed are sodium nitrite, n-butyl nitrite and tert-butyl nitrite. Second approach is to use Lewis acid such as zinc chloride, aluminium chloride, tin chloride, stannous and stannic chloride in a solvent or mixture of solvents compatible with Lewis acids. Significant yield and purity can be obtained when zinc chloride is employed as Lewis acid in presence of methanol. Third approach is to use activated charcoal in suitable alcoholic solvent. Aromatization was found to be effective in methanol as solvent along with activated charcoal.

In an embodiment of the present invention, in step-a, aromatization of compound of the formula (II) to compound of the formula (I) is also effective even in presence of oxygen without using activated charcoal in alcoholic solvents such as methanol, ethanol, isopropyl alcohol, ether solvents such as methyl tert-butyl ether, tetrahydrofuran, etc.

In another embodiment of the present invention, step-b is carried out in dichloromethane or dichloroethane as a solvent and diisopropylethyl amine as a base. Catalyst used are sodium hydrogen sulphate, potassium hydrogen sulphate along with ammonium thiocyanate to obtain compound of formula (II), wherein the optimum temperature range for the reaction is −5 to 30° C.

In another embodiment of the present invention, step-c is carried out in methanol as a solvent. Reaction is carried out in methanol at 75-85° C. and hydrochloride salt was prepared in ethyl acetate at 20-25° C.

The Scheme of the process of the present invention is as follows:

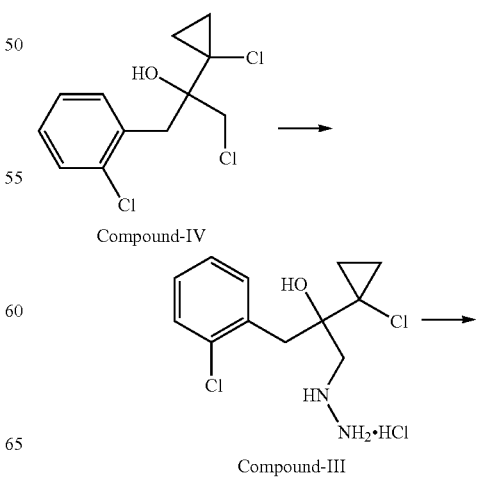

Compound-IV

Compound-III

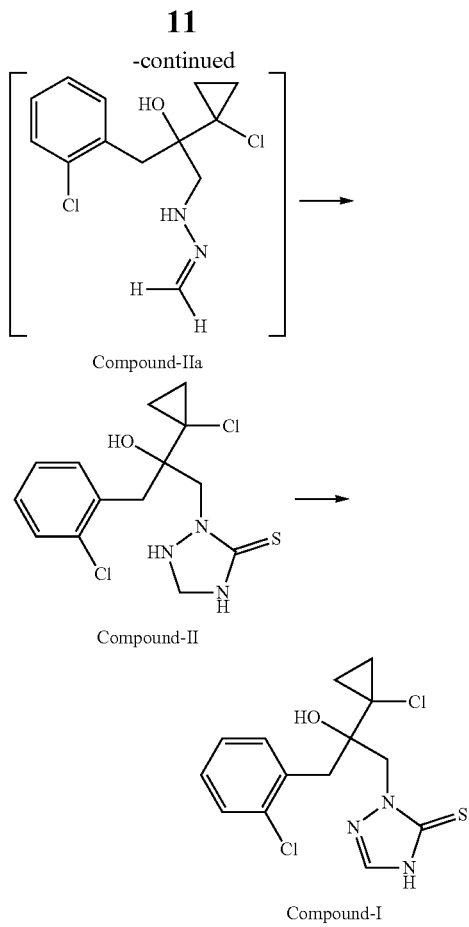

Compound-IIa

Compound-II

Compound-I

The compound of the formula (I) can be further purified by standard methods, for example, by recrystallization using a suitable solvent. A suitable solvent is selected from non-polar hydrocarbon; mixture of non-polar hydrocarbon such as pentane, hexanes, heptane and octane; polar protic solvents such as methanol, ethanol, isopropyl alcohol, n-butyl alcohol, tert-butyl alcohol, pentanol; mixture of non-polar hydrocarbons with polar protic solvents such as mixture of heptane and isopropyl alcohol, heptane and ethanol at temperature ranges from −5° C. to 82° C.

In another embodiment of the present invention, the solvent used for recrystallization of compound of formula (I) (Prothioconazole) is methanol and the temperature ranges from −5 to 82° C.

The examples below serve to illustrate the invention and are not to be understood as limiting it.

EXAMPLES

Example 1

Step 1: Preparation of Compound of Formula (III):

To a mixture of compound of the formula (IV) (125 g, 0.44 mol) in methanol (1250 ml, 10 T/v) was added hydrazine hydrate (224 g, 125 ml, 4.47 mol) at 20-30° C. The reaction mixture was stirred at 75-80° C. for 4-5 hours. Progress of the reaction was monitored by HPLC. On completion of the reaction, reaction mixture was cooled to 20-30° C. The reaction mixture was slowly poured into water (1250 ml, 10 T/v) at 20-30° C. Resulting suspension was stirred for 1-2 hours at 20-30° C. The product was filtered, washed with methanol (125 ml, 1 T/v), and suck-dried for 20-35 min under vacuum at 20-30° C. The solid was dissolved in ethyl acetate (1250 ml, 10 T/v). Sodium sulphate (125 g, 1 T/w) was added to ethyl acetate. Inorganics were filtered off and washed with ethyl acetate (125 ml, 1 T/v). Hydrogen chloride gas was bubbled for 1-1.5 hours at 20-30° C. The resulting precipitate was stirred for 20-30 min at 20-30° C. The product was separated by filtration and was washed with ethyl acetate (125 ml, 1 T/v). The product was dried at reduced pressure at 20-30° C. until constant weight was obtained. The compound of the formula (III) (53 g) was obtained in 90% yield and 98% purity.

Step 2: Preparation of Compound of Formula (II):

To a suspension of compound of the formula (III) (25 g, 0.08 mol) in dichloromethane (250 ml, 10 T/v) was slowly added N,N-diisopropylethylamine (12.4 g, 0.096 mol) at 20-30° C. To the reaction mixture was added aq. formaldehyde solution (strength: 37-41%, 2.4 g, 0.080 mol) slowly at −5 to 0° C. The reaction mixture was stirred for 1 hour at −5 to 0° C. Ammonium thiocyanate (6.11 g, 0.12 mol) and potassium hydrogen sulphate (19.6 g, 0.14 mol) were added to the reaction mixture at −5 to 0° C. The reaction mixture was stirred for 1-2 hours at 20-30° C. The progress of the reaction was monitored by HPLC. Upon completion of the reaction, DM water (250 ml, 10 T/v) was added to the reaction mixture at 20-30° C. Aq. layer was re-extracted with dichloromethane (125 ml, 5 T/v). Combined dichloromethane layer was washed with 5% aqueous sodium chloride (50 ml, 2 T/v) at 20-30° C. Dichloromethane was recovered at reduced pressure at 40-45° C. to obtain crude compound of the formula (II). Methanol (50 ml, 2 T/v) was added to the crude compound of the formula (II) at 20-30° C. The resulting precipitate was stirred for 20-30 min at 20-30° C. The product was separated by filtration and was washed with methanol (12.5 ml, 0.5 T/v). The product was dried at reduced pressure for 1-2 hours at 20-30° C. until constant weight is achieved. The pure compound of the formula (II) (20 g) was obtained in 72% yield and 96% purity by HPLC.

Step-3: Preparation of Compound of Formula (I):

Compound of formula (II) (5 g, 0.014 mol) was dissolved in methanol (50 ml, 10 T/v) at 50-55° C. Activated charcoal (5 g) was added at 50-55° C. The solution was cooled and stirred for 22-24 h at 20-30° C. The progress of reaction was monitored by HPLC. Upon completion of reaction, charcoal was filtered off through celite and washed with methanol (5 ml, 1 T/v). Methanol was evaporated at reduced pressure at 40-45° C. to give crude Prothioconazole. (4.2 g, 84% yield, purity: 96% by HPLC).

Crude Prothioconazole (4.2 g) was suspended in solution of diisopropyl ether in n-heptane (25 ml, 6.25 T/v, 1:9) for 1 h at 20-30° C. product was filtered and washed with solution of diisopropyl ether in n-heptane (4 ml, 1:9). Product was dried at reduced pressure for 1 h at 20-30° C. The pure compound of the formula (I) (4 g) was obtained in 80% yield and 98% purity by HPLC.

Example-2: Preparation of Compound of Formula (I) Using Oxidizing Agent Hydrogen Peroxide To a solution of compound of formula (II) (0.5 g, 0.00145 mol) in dichloromethane (5 ml, 10 T/v) was charged acetic acid or formic acid at 20-30° C. Reaction mass was cooled to 0-5° C. and charged hydrogen peroxide (0.146 g, 0.0043 mol) at 0-5° C. Reaction mass was stirred for 2-4 hours at 0-5° C. and continued for 12-15 h at 20-30° C. The progress of reaction was monitored by HPLC analysis. After completion of reaction, reaction mass was washed with 10% aq.

Sodium hydrogen carbonate (10 ml, 20 T/v) followed by washing with water (10 ml, 20 T/v) and brine (10 ml, 20 T/v). Organic phase was dried over sodium sulphate, filtered and concentrated under reduced pressure. This gives 0.35 g of compound of formula (I) which according to HPLC analysis, comprises 65% of compound of formula (I).

Example-3: Preparation of Compound of Formula (I) Using Oxidizing Agent Sodium Nitrite To a solution of compound of formula (II) (0.83 g, 0.0023 mol) in methanol was added conc. hydrochloric acid (0.71 g, 0.0069 mol) at 0-5° C. Solution of sodium nitrite (0.158 g, 0.0023 mol) in water (2 ml, 2.4 T/v) was added drop wise at 0-5° C. The reaction was continued for 1-2h at 0-5° C. The progress of reaction was monitored by HPLC analysis. Upon completion of reaction, methanol from reaction mass was distilled off under reduced pressure at 30-40° C. Residue was dissolved in ethyl acetate (15 ml, 18T/v) and was washed with 10% sodium bicarbonate solution (15 ml, 18T/v), water (15 ml, 18T/v) and brine solution (15 ml, 18T/v). Organic phase was dried over sodium sulphate, filtered and concentrated under reduced pressure. This gives 0.75 g of compound of formula (I) which according to HPLC analysis, comprises 78% of compound of formula (I).

Example-4: Preparation of Compound of Formula (I) Using Oxidizing Agent Copper Sulphate Pentahydrate To a solution of compound of formula (II) (0.5 g, 0.00145 mol) in methanol (10 ml, 20 T/v) was charged copper sulphate pentahydrate (0.54 g, 0.0021 mol) at 20-30° C. The reaction mass was stirred for 4 h at 20-30° C. The progress of reaction was monitored by HPLC analysis. Upon completion of reaction, methanol from reaction mass was distilled off under reduced pressure at 40-45° C. Residue was dissolved in ethyl acetate (15 ml, 30 T/v) and washed with water (15 ml, 30 T/v) and brine solution (15 ml, 30 T/v). Ethyl acetate layer was dried over sodium sulphate, filtered and concentrated under reduced pressure. This gives 0.35 g of compound of formula (I) which according to HPLC analysis, comprises 72% of compound of formula (II).

Example-5: Preparation of Compound of Formula (I) Using Lewis Acid Zinc Chloride To a solution of compound of formula (II) (0.2 g, 0.00057 mol) in methanol (10 ml, 20 T/v) was charged zinc chloride (0.1 g, 0.00073 mol) at 20-30° C. The reaction mass was stirred for 6 h at 20-30° C. The progress of reaction was monitored by HPLC analysis. Upon completion of reaction, methanol from reaction mass was distilled off under reduced pressure at 40-45° C. Residue was dissolved in ethyl acetate (15 ml, 30 T/v) and washed with water (15 ml, 30 T/v) and brine solution (15 ml, 30 T/v). Ethyl acetate layer was dried over sodium sulphate, filtered and concentrated under reduced pressure. This gives 0.15 g of compound of formula (I) which according to HPLC analysis, comprises 78% of compound of formula (II).

Example-6: Preparation of Compound of Formula (I) Using Lewis Acid Tin (II) Chloride (Stannous Chloride)

To a solution of compound of formula (II) (0.2 g, 0.00057 mol) in methanol (10 ml, 20 T/v) was charged tin (II) chloride (stannous chloride) (0.129 g, 0.00061 mol) at 20-30° C. The reaction mass was stirred for 8 h at 20-30° C. The progress of reaction was monitored by HPLC analysis. Upon completion of reaction, methanol from reaction mass was distilled off under reduced pressure at 40-45° C. Residue was dissolved in ethyl acetate (15 ml, 30 T/v) and washed with water (15 ml, 30 T/v) and brine solution (15 ml, 30 T/v). Ethyl acetate layer was dried over sodium sulphate, filtered and concentrated under reduced pressure. This gives 0.13 g of compound of formula (I) which according to HPLC analysis, comprises 68% of compound of formula (II).

Example-7: Preparation of Compound of Formula (I) Using Oxygen Without Using Activated Charcoal Compound of formula (II) (5 g, 0.014 mol) was dissolved in methanol (50 ml, 10 T/v) at 50-55° C. Reaction mixture was cooled to 0-5° C. Oxygen gas was purged for 4-6 h at 0-5° C. Reaction mixture was stirred for 8-10 h at 20-30° C. The progress of reaction was monitored by HPLC. Upon completion of reaction, methanol was evaporated at reduced pressure at 40-45° C. to give crude Prothioconazole. (4.8 g, 96% yield, purity: 96% by HPLC).

Crude Prothioconazole (4.8 g) was suspended in solution of diisopropyl ether in n-heptane (25 ml, 6.25 T/v, 1:9) for 1 h at 20-30° C. Product was filtered and washed with solution of diisopropyl ether in n-heptane (4 ml, 1:9). Product was dried at reduced pressure for 1 h at 20-30° C. The pure compound of the formula (I) (4.3 g) was obtained in 86% yield and 98% purity by HPLC.

Comparative Data

| Compound of formula (III) | | | |
| --- | --- | --- | --- |
| | Yield (%) | Purity (%) | Reaction time |
| Present invention | 90 | 98 | Reaction: 4 h at 75-80° C., HCL salt preparation: 1-2 h at room temp. |
| Example 1 of US2003/013890 | 95.9 | 97.9 | Reaction: 4 h at 85° C., HCL salt preparation: 16 h at room temp. |
| Comparative example A of US2003/013890 | 94.5 | 86.8 | Reaction: 5 h at 100° C., |

| Compound of formula (II) | | | |
| --- | --- | --- | --- |
| | Yield (%) | Purity (%) | Reaction time |
| Present invention | 72 | 96 | 1-2 h at 20-30° C. |
| Example 1 of US2003/013890 | 94.08 | 80.35 | 2-3 h at room temp. |
| Comparative example A of US2003/013890 | Not reported | 86.9 | 3 h at 60° C. |

| Compound of formula (I) | | | |
|---|---|---|---|
| | Yield (%) | Purity (%) | Reaction time |
| Present invention | 80 | 98 | 8-10 h at 20-30° C. |
| Example 1 of US2003/013890 | 99.2 | 94.8 | 6 h at room temp. |
| Example 2 of US2003/013890 | 98.2 | 97.1 | 2 h at room temp. |
| Comparative example A of US2003/013890 | Not reported | 71 | 3.5 h at 70° C. |

The invention claimed is:

1. A process for the preparation of compound of formula (I)

Compound-I

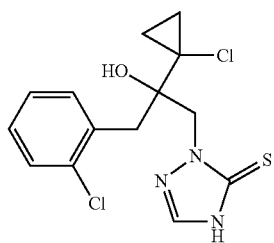

comprising the steps of:
i) reacting compound of the formula (IV) with hydrazine hydrate in alcoholic solvent to obtain compound of formula (III);
ii) isolating compound of formula (III) obtained in step i) in its hydrochloride salt form:

Compound-IV

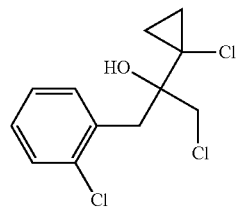

Compound-III

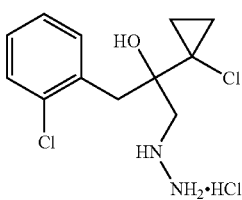

iii) reacting compound of the salt form of formula (III) obtained in step (ii) with aqueous formaldehyde solution in presence of a suitable solvent or a mixture of solvents and organic base at temperature between −5 and 35° C. to obtain compound of formula (IIa), which on treatment with thiocyanate in presence of a catalyst and solvent at temperature between −5 and 35° C. to obtain crude compound of formula (II);

Compound-IIa

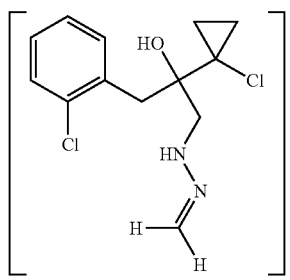

Compound-II

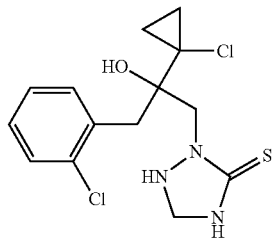

iv) purifying crude compound of the formula (II) obtained in step iii) using alcoholic solvents;
v) aromatization or oxidizing compound of formula (II) obtained in step (iv) in presence of a suitable solvent or a mixture of solvents at a temperature between −10 and 75° C. to obtain a crude compound of formula (I);
vi) purifying crude compound of the formula (I) obtained in step v) using suitable solvents or mixtures of suitable solvents.

2. The process as claimed in claim 1, wherein the alcoholic solvent used in step (i) is selected from methanol, ethanol, and isopropyl alcohol.

3. The process as claimed in claim 1, wherein the agent used for salt formation of compound of formula (III) in step (ii) is hydrochloric acid.

4. The process as claimed in claim 1, wherein the solvent used in step (iii) is selected from dichloromethane (DCM), ethylene dichloride (EDC), ethyl acetate, butyl acetate, isopropyl acetate; toluene, xylene, chloro benzene or mixtures thereof.

5. The process as claimed in claim 1, wherein the organic base used in step (iii) is selected from pyridine, N-methyl morpholine, triethylamine (TEA) and diisopropylethylamine.

6. The process as claimed in claim 1, wherein thiocyanate used in step (iii) is selected from sodium thiocyanate, potassium thiocyanate, and ammonium thiocyanate.

7. The process as claimed in claim 1, wherein the catalyst used in step (iii) is selected from sodium hydrogen sulphate and potassium hydrogen sulphate.

8. The process as claimed in claim 1, wherein the alcoholic solvent used for purification of the compound of the formula (II) in step (iv) is selected from methanol, ethanol, and isopropyl alcohol.

9. The process as claimed in claim 1 wherein aromatization in step (v) is carried out in the presence of Lewis acid selected from stannous chloride, and zinc chloride.

10. The process as claimed in claim 1 wherein aromatization in step (v) is carried out in the presence of activated charcoal.

11. The process as claimed in claim 1 wherein aromatization in step (v) is carried out by purging oxygen into the reaction mixture.

12. The process as claimed in claim 1, wherein the solvent used in step (v) is selected from ethyl acetate, isopropyl acetate, butyl acetate; methanol, ethanol, n-propanol, isopropyl alcohol or mixtures thereof.

13. The process as claimed in claim 1 wherein the solvent used for purification of compound of formula (I) in step (vi) is selected from hexane, heptane, methanol, ethanol, isopropyl alcohol or mixtures thereof.

* * * * *